United States Patent [19]
Bruenn et al.

[11] Patent Number: 5,831,013
[45] Date of Patent: Nov. 3, 1998

[54] CAPSID POLYPEPTIDES AND USE TO INHIBIT VIRAL PACKAGING

[75] Inventors: Jeremy A. Bruenn, Buffalo; Wensheng Yao, Kenmore, both of N.Y.

[73] Assignee: The Research Foundation of State University of New York, Amherst, N.Y.

[21] Appl. No.: 674,351

[22] Filed: Jul. 2, 1996

[51] Int. Cl.$^6$ .................................................. A01N 63/00
[52] U.S. Cl. ..................... 530/350; 424/93.2; 435/69.1; 435/172.3; 435/252.3; 530/826
[58] Field of Search .................................... 530/350, 826; 424/93.2; 435/69.1, 172.3, 252.3

[56] References Cited

U.S. PATENT DOCUMENTS

| | | |
|---|---|---|
| 4,970,168 | 11/1990 | Tumer . |
| 5,185,253 | 2/1993 | Tumer . |
| 5,304,730 | 4/1994 | Lawson et al. . |

OTHER PUBLICATIONS

Valle, R.P.C. and Wickner, R.B., *J. of Virology*, 67(5):2764–2771 (1993).
Wickner et al., *J. of Virology*, 65(1):155–161 (1991).
Park et al., *Virology*, 218:451–454 (1996).
Yao et al., *J. of Virology*, 69(3):1917–1919 (1995).
Lindbo, J.A. and Dougherty, W.G., *Virology*, 189:725–733 (1992).
Lindbo, J.A. and Dougherty, W.G., *Molecular Plant Microbe Interat.*, 5(2):144–153 (1992).
Diamond et al., *J. of Virology*, 63(9):3983–3990 (Sep. 1989).
Yao, W. and Bruenn, J.A., *Virology*, 214:215–221 (1995).

*Primary Examiner*—Laurie Scheiner
*Attorney, Agent, or Firm*—Jaeckle Fleischmann & Mugel, LLP; Susan J. Braman, Esq.

[57] ABSTRACT

The present invention is directed to a viral capsid polypeptide capable of inhibiting viral packaging, the viral capsid polypeptide consisting of a portion of a viral capsid protein of an RNA virus and including a multimerization domain of the viral capsid protein. The invention further provides an isolated nucleic acid molecule encoding such a viral capsid polypeptide. Expression vectors and host cells comprising the nucleic acid molecules are also provided, as well as a method for inhibiting viral packaging in a host cell by expressing the viral capsid polypeptide. In two preferred embodiments, the RNA virus is the ScVL1 virus or the ScVLa virus of Saccharomyces cerevisiae.

3 Claims, 1 Drawing Sheet

ScV cap

Region required for interference 1        203   275   335      448    473           680
        (202)(264)(324)   (442)   (443)

La cap-L1 cap similarity

VP3 similarity

Fig. 1

CAPSID POLYPEPTIDES AND USE TO INHIBIT VIRAL PACKAGING

The subject matter of this application was made with support from the United States Government under grant MCB9106818 of the National Science Foundation and grant GM22200 of the National Institutes of Health.

FIELD OF THE INVENTION

The present invention relates generally to capsid polypeptides, and more particularly to a viral capsid polypeptide which is capable of inhibiting viral packaging. The viral capsid polypeptide consists of a portion of a viral capsid protein of an RNA virus and includes a multimerization domain of the viral capsid protein.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

A virus is a genetic element that contains either deoxyribonucleic acid (DNA) or ribonucleic acid (RNA), that can alternate between an intracellular state and an extracellular state. In either state, viruses are submicroscopic particles containing nucleic acid surrounded by protein and occasionally containing other components. Viruses can vary widely in size, shape, chemical composition, range of organisms attacked, kinds of cell damage induced, and range of genetic capabilities. Viruses are known to infect animals, plants, bacteria, and fungi.

An analysis of the chemical structure of viruses shows that some contain RNA and others DNA. The DNA molecules of many viruses are double stranded (dsDNA), but some have single stranded DNA (ssDNA). While the RNA molecules of most RNA viruses are single stranded (ssRNA), a few viruses with double stranded RNA (dsRNA) are known.

The structure (size and shape) of viruses are exceedingly diverse. The internal structure of viruses, however, generally has the nucleic acid located in the center surrounded by a protein coat called the capsid. The individual proteins that make up the capsid are called protein subunits, or capsomeres.

Replication of viruses requires that the virus induce a living cell of a host organism to make more of the essential components needed by the virus particle for growth. These components must then be assembled in the proper order and the new virus particles must escape from the cell and infect other cells. The various phases of this replication process can be summarized as: 1) attachment (adsorption) of a virus particle to a sensitive cell; 2) penetration into the cell by the virus or its nucleic acid; 3) replication of the viral nucleic acid; 4) production of capsid protein and other essential viral constituents; 5) assembly of nucleic acid and capsid protein into new virus particles (or packaging of the virus particle); and 6) release of mature virus particles from the cell.

With this life cycle (replication process) of a virus in mind, one should be able to attack the progression of viral infection in an animal, plant, bacteria or fungi by interfering with (or inhibiting) any of the stages of the viral life cycle essential to viral replication. Given the severity of many viral infections, in all types of hosts, a need always exists for new methods of inhibiting viral replication as a means of treating and/or preventing deleterious viral infections. Examination of particular viruses could lead to the discovery of such methods, which in turn could lead to the elucidation of a method applicable to all or nearly all viruses.

Several methods have been explored to interfere with viral replication. Recently, considerable attention has been focused on the capsid proteins (also called coat proteins, cap or gag). These proteins form one of the major structural components of the virus particles and hence are ideal as possible targets for viral interference. It has been observed that over expression of full-length viral coat proteins results in inhibition of viral replication. This phenomenon is well documented in plant cells. U.S. Pat. Nos. 4,970,168 and 5,185,253 to Tumer disclose a method for producing transgenic plants that are resistant to Potato virus X and Potato virus Y, by inserting a gene encoding the full length coat protein into the plant's genome. U.S. Pat. No. 5,304,730 to Lawson et al. discloses a DNA sequence encoding a potato leafroll virus (PLRV) coat protein that can be used to confer resistance to PLRV. Each of the above patents discloses expression of the full length coat protein of a plant virus in order to confer resistance to that virus.

Recently, persistent viral infections have been encountered in yeast cultures of *Saccharomyces cerevisiae*. This yeast is commonly used in fermentation processes and has gained significant recognition as an expression system for producing high levels of recombinant proteins. As a result, this yeast expression system is currently being used for producing certain vaccines. For example, yeast-derived recombinant hepatitis B vaccines have replaced plasma-derived hepatitis B vaccines in the United States.

Two double stranded RNA viruses are known to exist as permanent infections of the yeast *Saccharomyces cerevisiae*. These viruses, ScVL1 and ScVLa, are totiviruses. that is, dsRNA viruses in which all viral functions are encoded on a single segment of dsRNA. In the literature, L1 is synonymous with L-A, and La is synonymous with L-BC (Bruenn, 1988). Each has two large open reading frames, cap (encoding the viral capsid protein Cap) and pol (encoding the viral RNA-dependent RNA polymerase, or RDRP, Pol). The two open reading frames overlap and the pol region is translated as a Cap-Pol fusion by translational frameshifting (Diamond et al., 1989; Tu et al., 1992; Tzeng et al., 1992). Totivirus particles (including ScVL1) are icosohedral, in which 120 copies of Cap are arranged in 12 pentameric units (Cheng et al., 1994). ScVL1 and ScVLa are related viruses (Bruenn, 1993) that do not package each other's RNA (El-Sherbeini et al., 1984; Reilly et al., 1984; Thiele et al., 1984).

Due to the important uses of *Saccharomyces cerevisiae*, it would be beneficial to find ways to confer resistance in this organism to the ScVL1 and ScVLa viruses. In this regard, Valle and Wickner have shown that overexpression of both full-length Cap and Cap-Pol proteins interferes with maintenance of ScVL1, which is then lost from the cells (Valle and Wickner, 1993).

Recently, it has also been shown that overproduction of full length La Cap alone interferes with ScVLa replication (Yao et al., 1995). However, overproduction of full length L1 Cap increases the viral copy number of ScVL1 (Wickner et al., 1991). Expression of cDNA clones of fragments of viral capsid proteins was shown to be an effective means of conferring resistance to a virus (Lindbo and Dougherty, 1992*a*). This resistance, however, appeared to be mediated by RNA-RNA interactions (Lindbo and Dougherty, 1992*b*) and the production of peptide fragments encoded by the cDNA fragments of the full length viral capsid protein did not occur.

Since it is more efficient to work with shorter DNA segments, a need continues to exist for new and/or improved methods and means for treating and/or preventing viral infection using shorter DNA segments. Methods and means which inhibit viral packaging can provide one answer to this need.

SUMMARY OF INVENTION

To this end, the subject invention provides a viral capsid polypeptide capable of inhibiting viral packaging, the viral capsid polypeptide consisting of a portion of a viral capsid protein of an RNA virus and including a multimerization domain of the viral capsid protein. The invention further provides an isolated nucleic acid molecule encoding such a viral capsid polypeptide. In one embodiment, the RNA virus is the ScVL1 virus of *Saccharomyces cerevisiae*, and in another embodiment the RNA virus is the ScVLa virus of *Saccharomyces cerevisiae*.

The isolated nucleic acid molecules of the invention can be inserted into suitable expression vectors and/or host cells. Expression of the nucleic acid molecules encoding the viral capsid polypeptides results in production of the encoded polypeptide which inhibits viral packaging in the host cell.

The invention thus also provides a method of inhibiting viral packaging in a host cell, which comprises introducing the nucleic acid molecules of the subject invention into the cell and allowing the cell to express the nucleic acid molecules. This results in inhibition of viral packaging in the cell. The packaging of yeast, plant, and mammalian viruses can thus be inhibited in cells, such as the yeast, plant, and mammalian cells, respectively, infected by these viral pathogens. By inhibiting viral packaging, the viral "particles" are not packaged and cannot complete their life cycle, and therefore cannot move on to infect subsequent cells.

BRIEF DESCRIPTION OF THE DRAWINGS

These and other features and advantages of this invention will be evident from the following description of preferred embodiments when read in conjunction with the accompanying drawing in which:

FIG. 1 shows the location of the region required for interference in L1 and La Cap. Residues without parentheses refer to L1 Cap and residues with parentheses refer to La Cap. Alignments were performed with gap (Devereux et al., 1984). The region similar to the picornavirus vp3 was described previously (Bruenn et al., 1989).

DETAILED DESCRIPTION

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence as the molecule in item 1 but not necessarily separated from the organism (i.e. synthesized nucleic acid molecules), or 3) a nucleic acid molecule which is a portion of the molecule of item 1 or a portion of the molecule of item 2. A "portion" refers to part of the entire molecule, that part being, for example, between about 60% and about 70% of the entire molecule, and preferably between about 63% and about 69% of the entire molecule.

As further used herein, the terms "corresponding to" or "having" or "as shown in" or "consisting of" when used in conjunction with a SEQ ID NO for a nucleotide sequence refer to a nucleotide sequence which is substantially the same nucleotide sequence, or derivatives thereof (such as deletion and hybrid variants thereof, splice variants thereof, etc.) Nucleotide additions, deletions, and/or substitutions, such as those which do not affect the translation of the DNA molecule, are within the scope of a nucleotide sequence corresponding to or having or as shown in or consisting of a particular nucleotide sequence (i.e. the amino acid sequence encoded thereby remains the same). Such additions, deletions, and/or substitutions can be, for example, the result of point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting viral capsid polypeptide. These are also within the scope of a nucleotide sequence corresponding to or having or as shown in or consisting of a particular nucleotide sequence.

Similarly, the term "corresponding to" or "having" or "as shown in" or "consisting of" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the resulting polypeptide to inhibit viral packaging are within the scope of an amino acid sequence corresponding to or having or as shown in or consisting of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residue, which includes histidine, lysine, and arginine. Leucine, isoleucine, valine, and methionine, all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French and Robson 1983, Taylor 1986, and Bordo and Argos 1991.

As further used herein, the term "corresponding to" or "having" or "as shown in" or "consisting of" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotide or amino acids within the recited sequence For example, those skilled in the art will readily understand than an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations As a further example, those skilled in the art will readily understand that an asparagine residue could be replaced with an ethylasparagine if an ethyl side chain is desired, a lysine residue could be replaced with a hydroxy-lysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified nucleotides and amino acids.

With these definitions in mind, the subject invention provides an isolated purified viral capsid polypeptide capable of inhibiting viral packaging. The viral capsid polypeptide consists of a portion of a viral capsid protein of an RNA virus and includes the multimerization domain of the viral capsid protein. Preferably, the viral capsid polypeptide extends from the amino terminal of the viral capsid protein through to the carboxy terminal of the multimerization domain of the viral capsid protein. The multimerization domain of the viral capsid protein may, in one embodiment, have an eight-fold beta barrel structure.

A beta barrel structure of a capsid protein refers to the portion of the protein which forms a beta barrel tertiary structure. The amino acid sequence of the capsid protein is the protein's primary structure, and the protein's secondary structure is the three dimensional structure of the protein (for example, an alpha helix, or a beta-sheet, or a beta-turn). The individual secondary structural elements of the protein next associate to form the protein's tertiary structure The tertiary structure reflects the interactions between the amino acid side chains, as well as between amide bonds, of the protein. Two examples of general classifications of tertiary structure include helix bundles and beta barrels. Proteins may also self-assemble into multimeric forms that stabilize their tertiary structure The orientation of individual monomers as a multimeric protein is referred to as the quaternary structure, and the portion of each protein involved in the formation of such multimers is referred to as a multimerization domain.

RNA viruses which have viral capsid proteins which include a multimerization domain are numerous. These RNA viruses include yeast, plant, and mammalian viruses. For example, there are two viruses of the yeast *Saccharomyces cerevisiae* which have a viral capsid protein (Cap) which includes a multimerization domain in its quaternary structure. These two viruses are ScVL1 and ScVLa. Further descriptions of RNA viruses with multimerization domains, and in particular those with a beta barrel structure, can be found in Getzoff et al. 1986, Chelvanayagam et al. 1992, and Rossmann 1987.

To explain the concept and meaning of multimerization domains and beta barrels further, a similarity had been observed between the picornavirus vp3 protein and a region of the cap protein of a *Saccharomyces cerevisiae* virus (Bruenn et al. 1989). In the subset of viruses with icosahedral symmetry, there is extensive secondary and tertiary structural homology among the viral capsid proteins. All have one or more capsid proteins with an eight stranded anti-parallel beta-barrel structure (Rossmann, 1987). In most of the plant viruses, such as tomato bushy stunt virus (TBSV), Southern bean mosaic virus (SBMV), turnip yellow mosaic virus (TYMV), and brome mosaic virus (BMV), the capsid is composed of 180 copies of one such protein of about 30 kilodaltons, in which a central S domain of about 190 amino acids adopts the beta-barrel structure. These viruses have a T=3 symmetry. The small plus strand animal viruses, the picornaviruses, such as foot and mouth disease virus (FMDV), poliovirus (polio), human rhinovirus (HRV), encephalomyocarditis virus (EMC), and Mengovirus (Mengo) have a pseudo T=3 structure. Their icosahedral faces have three different capsid proteins, each of about 250 amino acids: VP1, VP2, and VP3. These are of different primary sequence but essentially have identical protein folding, and replace the three proteins of identical sequence present on each face of the T=3 plant virus capsid. There is no detectable primary sequence similarity between the T=3 plant virus capsid proteins and the picornavirus capsid proteins, but the structural homology between them and the S domain is striking (Rossmann, 1987). These beta barrel structures, where determined, form a part of the multimerization domain of the capsid protein.

The capsid proteins of the plant and animal RNA viruses for which X-ray crystal structures exist have been compared by a process of three-dimensional mapping. This analysis demonstrates that the proportion of structurally equivalent residues is highest for VP3 versus the plant virus capsid proteins (Rossmann, 1987). Among the picornaviruses, VP3 also shows the greatest conservation. For instance, the VP3 of Mengovirus is more than 90° structurally identical to the VP3 of HRV14 (Rossmann, 1987), while they share only about 48° amino acid sequence similarity. Although there is no X-ray structure for the alphavirus Sindbis (SNBV), high resolution electron microscopy has demonstrated a T=3 symmetry for the nucleocapsid. The single viral nucleocapsid protein, of 264 amino acids, has detectable sequence similarity to the picornavirus VP3.

A multimerization domain and a beta barrel structure, as used herein, are as described above.

ScVL1 and ScVLa are two examples of RNA viruses whose capsid proteins include a multimerization domain. The nucleotide and amino acid sequences of ScVL1 are known (see Diamond et al. 1989), and are provided herein as SEQ ID NO:1 (nucleotide) and SEQ ID NO:2 (amino acid sequence of the cap protein). The viral capsid polypeptide of the subject invention is encoded by nucleotides 30 to 1421 of SEQ ID NO:1 (amino acids 1 to 473 of SEQ ID NO:2). This viral capsid polypeptide is capable of inhibiting packaging of the ScVL1 virus in *Saccharomyces cerevisiae*, and the sequence of the polypeptide consists of a portion (473 of 680 amino acids or about 70%) of the Cap protein of ScVL1, and includes the multimerization domain (about amino acids 203–448).

The nucleotide and amino acid sequences of ScVLa are also known (see Park et al. 1996), and are provided herein as SEQ ID NO:3 (nucleotide) and SEQ ID NO:4 (amino acid sequence of the cap protein). The viral capsid polypeptide of the subject invention is encoded by nucleotides 24 to 1352 of SEQ ID NO:3 (amino acids 1 to 443 of SEQ ID NO:4). This viral capsid polypeptide is capable of inhibiting packaging of the ScVLa virus in *Saccharomyces cerevisiae*, and the sequence of the polypeptide consists of a portion (443 of 697 amino acids or about 64%) of the Cap protein of ScVLa, and includes the multimerization domain (about amino acids 202–442).

The subject invention further provides an isolated nucleic acid molecule encoding a viral capsid polypeptide capable of inhibiting viral packaging. The viral capsid polypeptide, as described above, consists of a portion of a viral capsid protein of an RNA virus and includes the multimerization domain of the capsid protein.

The nucleic acid molecule is preferably ribonucleic acid (RNA), and can be genomic or recombinant, biologically isolated or synthetic.

One embodiment of the nucleic acid molecule encoding a viral capsid polypeptide of the subject invention has a nucleotide sequence as shown in nucleotides 30 to 1421 of SEQ ID NO:1 (a nucleic acid molecule which encodes amino acids 1 to 473 of SEQ ID NO:2). This nucleic acid molecule encodes a viral capsid polypeptide which is capable of inhibiting packaging of the ScVL1 virus in Saccharomyces cerevisiae, and the sequence of the polypeptide consists of a portion (473 of 680 amino acids) of the Cap protein of ScVL1, and includes the multimerization domain (about amino acids 203–448).

Another embodiment of a nucleic acid molecule encoding a viral capsid polypeptide of the subject invention has a nucleotide sequence as shown in nucleotides 24 to 1352 of SEQ ID NO:3 (a nucleic acid molecule which encodes amino acids 1 to 443 of SEQ ID NO:4). This nucleic acid molecule encodes a viral capsid polypeptide which is capable of inhibiting packaging of the ScVLa virus in *Saccharomyces cerevisiae*, and the sequence of the polypeptide consists of a portion (443 of 697 amino acids) of the Cap protein of ScVLa, and includes the multimerization domain (about amino acids 202–442).

The nucleic acid molecules of the subject invention can be expressed in desirable host cells using conventional techniques. The viral capsid polypeptide encoded thereby can be expressed in any desirable host and can be introduced into the host by introducing the nucleic acid molecules directly into the host cells or by using a vector system to introduce the nucleic acid molecules. If it is desirable to inhibit viral packaging in mammalian tissue culture cells (for example, Hela cells, Cv-1 cells, COS cells) in vitro expression can be used. For other applications of the subject invention, in vivo expression can be used, for example to inhibit viral packaging in plant species and/or yeast species. For example, a plant can be stably transformed with the nucleic acid molecule of the subject invention which renders the plant resistant to a particular virus (by inhibiting packaging of that virus in the transformed plant). Seeds produced by that transformed plant could then be grown up to result in plants resistant to the virus.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells.

Various methods are known in the art for introducing nucleic acid molecules into host cells. One method is microinjection, in which nucleic acid is injected directly into the nucleus of cells through fine glass needles (RNA is injected directly into the cytoplasm of cells). Alternatively, nucleic acid can be incubated with an inert carbohydrate polymer (dextran) to which a positively charged chemical group (DEAE, for diethylaminoethyl) has been coupled. The nucleic acid sticks to the DEAE-dextran via its negatively charged phosphate groups. These large nucleic acid-containing particles stick in turn to the surfaces of cells, which are thought to take them in by a process known as endocytosis. Some of the nucleic acid evades destruction in the cytoplasm of the cell and escapes to the nucleus, where it can be transcribed into RNA like any other gene in the cell. In another method, cells efficiently take in nucleic acid in the form of a precipitate with calcium phosphate. In electroporation, cells are placed in a solution containing nucleic acid and subjected to a brief electrical pulse that causes holes to open transiently in their membranes. Nucleic acid enters through the holes directly into the cytoplasm, bypassing the endocytotic vesicles through which they pass in the DEAE-dextran and calcium phosphate procedures (passage through these vesicles may sometimes destroy or damage nucleic acid). Nucleic acid can also be incorporated into artificial lipid vesicles, liposomes, which fuse with the cell membrane, delivering their contents directly into the cytoplasm. In an even more direct approach, used primarily with plant cells and tissues, nucleic acid is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. In the subject invention, the viral capsid polypeptide for inhibiting viral packaging can be expressed in a cell by introducing the nucleic acid encoding the viral capsid polypeptide by use of another viral vector. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

The viral capsid polypeptide encoded by the introduced nucleic acid molecule will inhibit viral packaging in the host cell, thereby protecting the host cell from infection by the virus.

Various modifications of the nucleic acid and amino acid sequences disclosed herein are covered by the subject invention. These varied sequences still encode a functional viral capsid polypeptide (capable of inhibiting viral packaging).

The invention thus further provides an isolated nucleic acid molecule encoding a viral capsid polypeptide, the nucleic acid molecule encoding a first amino acid sequence having at least 90% amino acid identity to a second amino acid sequence, the second amino acid sequence selected from the group consisting of amino acids 1 to 473 of SEQ ID NO:2 and amino acids 1 to 443 of SEQ ID NO:4.

As indicated above, levels of the viral capsid polypeptide according to the subject invention can be expressed in a cell by introducing the nucleic acid molecule encoding the viral capsid polypeptide into the cell and by expressing the viral capsid polypeptide encoded thereby. For in vivo expression of viral capsid polypeptide, various gene therapy techniques can be utilized to get the nucleic acid molecule into the desired cell. In plants, for example, various plant specific promoters can be used as well as tissue specific promoters which permit expression of the viral capsid polypeptide in only those tissues that the promoter is "specific" for.

In certain circumstances, it may be desirable to administer the viral capsid polypeptide to a subject, in which case the polypeptide is provided in a composition with a suitable carrier. The compositions may be made up in any suitable form appropriate for the desired use; e.g., oral, parenteral, or topical administration. Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

In accordance with the above description of the subject invention, it should be readily apparent to those skilled in the art that it is possible to interfere with the replication of a number of RNA viruses by production of viral capsid polypeptides (such polypeptides being less than the entire capsid protein, and, in one preferred embodiment, being an amino terminal fragment of the entire capsid protein). Interference can occur by a number of mechanisms. The *Saccharomyces cerevisiae* double-stranded RNA viruses ScVL1 and ScVLa, which exist as permanent persistent infections of their host cells, can be cured very efficiently by production of N-terminal fragments of their capsid proteins. These totiviruses produce only two proteins: a capsid protein (Cap) and a Cap-Pol fusion protein with RNA-dependent RNA polymerase activity. Three types of interference can be detected: interference due to overproduction of both Cap and Cap-Pol, interference due to overproduction of Cap (and consequent distortion of the Cap to Cap-Pol ratio), and interference due to negative complementation by N-terminal fragments of Cap. Some N-terminal fragments of Cap appear to be incorporated into viral particles, but only in the presence of a complete Cap protein. Incorporation of N-terminal fragments of Cap can result in the formation of defective particles.

Vectors and strains

The vectors used for expression of cDNAs were pG1, with a yeast glucose-6-phosphate dehydrogenase promoter (Schena et al., 1991), or pG4 (see below). The original source of the full-size L1cDNA was the NIH. All other cDNA clones were derived by applicants. The assays for curing of ScVLa were in strain T120 (MATa mak10 trp1 ura3 La L1-0 M1-0) and those for curing of ScVL1 were in strain T141-3 (MATa trp1 leu2 his $Gal^+$ L1 M1 La-0) . T120 and T141 were both derived from a cross between BJ2169 (RPMI) and M179 (Yeast Genetics Stock Center). T141-3 was derived from T141 by curing of ScVLa with pGLa1 (see below) followed by loss of the plasmid by growth on nonselective media. Strain T141-4, used for expression of both Cap and truncated Cap proteins, was derived from T141-3 by curing of ScVL1 with pGL1d3 (see below) and curing of the plasmid by growth on nonselective media.

Transformation

Transformation of yeast was by the lithium acetate-polyethylene glycol method (Elbe, 1992), using selection for TRP1 or LEU2. Strains were always grown on selective media, to retain plasmids, unless otherwise stated.

Mutagenesis

Site-directed mutagenesis was of selected restriction fragments in $pGEM7Zf^+$, by the method of Kunkel (Kunkel, 1985). Every mutagenized fragment was completely sequenced before being returned to expression vector constructs for testing. Deletions were made by excising restriction fragments in $pGEM7Zf^+$and returning the truncated restriction fragments to expression vector constructs by using restriction sites in the multiple cloning sequence. Deletion mutants were made by incorporating restriction fragments of La or L1 cDNA clones containing their entire Cap genes, after blunt-ending with DNAP I Klenow fragment, into blunt-ended restriction sites in pG1 or its derivative pG4. Plasmid pG4 was constructed by replacing the BamHI-SalI region of pG1 with the sequence having SEQ ID NO:5: GATCTATAAAG<u>ATG</u>TCGGATCCCCC-GGGGGTACCGTCGAC, providing an AUG in the vector sequence (underlined). The La deletion constructs had the following bases from La (from SEQ ID NO:3): pGLa4, bases 16–2724; pGLa1, bases 16–2360; pGLa1d1, bases 16–1536; pGLa1d2, bases 16–1480; pGLa1d3, bases 16–1349; pGLa1d4, bases 16–1304; pGLa1d5, bases 16–1279; pGLa1d6, bases 16–1224; pGLa1d7, bases 58–1349; pGLa1d8, bases 315–1349. The L1 deletion constructs had the following bases from L1 (from SEQ ID NO:1): pGL1, bases 1–4571; pGL1d1, bases 1–2095; pGL1d2, bases 1–1835; pGL1d3, bases 1–1455; pGL1d4, bases 1–1332; pGL11d5, bases 1–1326. The nonsense mutants of La had bases 16–2360 of La (of SEQ ID NO:3); the nonsense mutants of L1 had bases 1–2095 of L1 (of SEQ ID NO:1). The nonsense mutants of L1 were pGLa1m3 (K506O), pGLa1m4 (I443O), pGLa1m5 (S419O), and pGLa1m6 (E11O), where O indicates ocher, and K506O indicates a change of a lysine at residue 506 to ocher. The nonsense mutants of L1 were pGL1m15 (G501O), pGL1m14 (Y485O), pGL1 m11 (F474O), pGL1m12 (E435O), and pGL1m13 (Q10O). The La sequence is in GenBank Accession No. U01060 and the L1 sequence is in GenBank Accession No. M28353 (Diamond et al., 1989).

RNA extraction and Northern hybridization

Crude RNA (including DNA) was prepared from whole cells by phenol extraction (Bruenn and Kane, 1978). These preparations have primarily dsRNA and the smaller single-stranded RNAs of the cell. For Northern analysis, total RNA was extracted with phenol and glass beads. Northern transfers of native RNA and hybridization to T7 or SP6 RNA transcripts of cDNAs were performed as described (Huan et al., 1991). Probes were made from pGEML1–4 (bases 1–521 of L1 [SEQ ID NO:1] in pGEM7Zf+) or pGEMLa1–6 (bases 16–487 of La [SEQ ID NO:3] in the same vector).

Western transfers

ScV particles were prepared by differential centrifugation and CsCl equilibrium gradient centrifugation as described (Shen and Bruenn, 1993). SDS-polyacrylamide gel electrophoresis (SDS-PAGE) and Western transfers were performed as previously described and probed with polyclonal antibodies to the ScVL1 Cap (Diamond et al., 1989). Crude protein extracts of cells were prepared by mechanical lysis as described (Sambrook et al., 1989) using 100 µl of buffer for a 10-ml culture at $OD_{550}=1$.

Killer assays

Detection of the ScVM1 phenotype (production of k1 killer toxin) was performed as described (Huan et al., 1991).

EXAMPLE I

Overproduction of Cap fragments interferes with ScVLa

An initial observation was that overproduction of La Cap from a cDNA expression vector resulted in curing of ScVLa (Yao et al., 1995). This is in contrast to what had been reported for ScVL1 (Valle and Wickner, 1993). In accordance with the subject invention, several deletion mutants lacking C-terminal portions of the La Cap were prepared and tested for their ability to cure ScVLa. Unexpectedly, all of these (pGLaldl-pGLa1d3) were at least as efficient at curing ScVLa as constructs containing the full-size La cap reading frame (see Table 1).

More particularly, the dsRNAs from a series of transformants expressing portions of the La Cap protein in a strain (T120) that originally had ScVLa (but no ScVL1) were elaborated on a 1 % agarose gel. The control (vector alone, pG1), the two nonsense mutants pGLa1m5 and m6, and the deletion pGLad5 did not interfere with ScVLa but the rest of the expression vector constructs did interfere.

The transformant colonies isolated after transformation with the expression plasmid were all cured of ScVLa after their initial 20 or so generations of growth to form a visible colony. Since the assay for the presence of ScVLa requires an RNA extraction, only 10 clones of each construct were tested. None retained ScVLa, while the control, with vector alone, always retained ScVLa. Previous constructs lacking small portions of the C-terminus of the La Cap did not interfere efficiently (Yao et al., 1995), but these had C-terminal substitutions from the L1 Cap, which apparently affect the La Cap interaction with wild-type La Cap monomers.

Several more constructs were made, in which increasingly larger deletions were made from the C-terminus of the La Cap, in order to determine which portion of the gene was required for interference. These experiments (Table 1) delimited the required region to the N-terminal 425 amino acids of La Cap, which is a protein of 697 amino acids (see SEQ ID NO:4). Removal of even a few amino acids from the N-terminus was fatal (Table 1). This interpretation of the data assumes that all the noninterfering constructs were properly transcribed, and this was verified by Northerns of nondenatured RNA.

Specifically; a 1.5% nondenaturing agarose gel of total RNA from transformants was denatured and transferred to nitrocellulose and probed with an La minus-strand probe. Those transformants not cured by the expression vectors (pG1, pGLa1m5 and m6, and pGLa1d5) still had La dsRNA. All other transformants were missing La, and all the transformants that should express La mRNA (including those that did not interfere with ScVLa) had several bands of La plus-strand transcript from the expression vector. The multiple bands were the result of alternate secondary structures of the RNAs, since a denaturing gel shows only one band. Note that progressively larger deletions (d1–d5) had smaller transcripts. Every construct was shown to be well-transcribed. The multiple bands of La transcript from the expression vector were the result of alternate secondary structures of the RNA, as shown by Northerns with denatured RNA.

In many cases, interference with viral replication can occur by production of interfering, untranslated viral RNAs (Fitchen and Beachy, 1993). For instance, this will work with ScVL1, by overproduction of its packaging signal (Huan et al, 1991; Shen and Bruenn, 1993). However, the region of La responsible for the interference observed here does not include its putative packaging signal. Nevertheless, another series of constructs were made that terminate La Cap synthesis with nonsense mutations, preserving the rest of the sequence intact. As expected, any mutant with a nonsense codon preceding the C-terminus of the essential region was incapable of interference, while mutants with nonsense codons C-terminal to the essential region were functional (Table 1). All of these mutants are normally transcribed as well. This is strong evidence that N-terminal fragments of the La Cap protein are responsible for the observed interference.

Experiments in which the presence of ScVLa is tested immediately after transformation with cDNA expression vectors demonstrate that interference with ScVLa (mirroring the situation with ScVL1) is much more effective with the N-terminal fragments of Cap than with the full-size Cap. As expected, La Cap or its N-terminal fragments do not interfere with ScVL1, and L1 Cap or its N-terminal fragments do not interfere with ScVLa.

EXAMPLE II

Overproduction of Cap fragments interferes with ScVL1

Given the sensitivity of ScVLa to overproduction of N-terminal fragments of its Cap protein, as well as the complete protein, it was surprising that ScVL1 was not sensitive to overproduction of its Cap protein. A number of deletion constructs of ScVL1 cap were prepared and overproduction of N-terminal fragments of the L1 Cap tested for their effect on ScVL1. Again, the N-terminal fragments interfered with ScVL1 (Table 1).

Specifically, the dsRNAs from a series of transformants expressing portions of the L1 Cap protein in a strain (T141-3) that originally had ScVL1 (but no ScVLa) were elaborated on a 1% agarose gel. Note that the constructs that did interfere with ScVL1 (L1d2 and L1d3) also eliminated ScVM1. The region responsible was mapped by deletions to the N-terminal 476 amino acids of L1 Cap, a protein of 680 amino acids (see SEQ ID NO:2) (Table 1). In this case, the initial screening assay for interference is the absence of the killer phenotype, which depends on ScVM1, whose dsRNA encodes a killer toxin, and whose replication depends on ScVL1. This provides a more facile assay, so more clones can be screened rapidly. The absence of ScVL1 and ScVM1 in the cured clones was verified by RNA extraction.

Dependence on the N-terminal fragments of Cap, rather than its RNA, was verified by making nonsense mutants of L1 cap (Table 1). However, none of the nonsense mutants of L1 cap (except when combined with deletions; see below) successfully interfered with ScVL1. This appears to be partially due to low steady-state mRNA levels in these expression constructs. Those L1 nonsense mutants that should interfere with viral particle assembly (L1m11, L1m14, L1m15) did not have significant steady-state levels of transcript, while the deletions (L1d1–L1d5) and the nonsense mutants that should not interfere (L1m12 and L1m13) all had reasonable levels of mRNA. The mutants L1m11, L1m14, and L1m15 did have reduced levels of L1 dsRNA present, as though interference was occurring but was not very efficient. As above, several bands of transcript were visible, and the deletions had progressively smaller mRNAs. The low levels of mRNA in those constructs that should interfere with ScVL1 (L1m11, L1m14, and L1m15) were correlated with a reduced amount of L1 dsRNA, as though interference was still occurring but was inefficient. However, the two nonsense mutants that should not interfere with ScVL1 (L1m12 and L1m13; as deduced from the results with the deletion mutants) did make levels of mRNA as high or higher than those of the deletion constructs that interfere (L1d2 and L1d3), so one may still conclude that interference requires Cap, not cap mRNA.

All of the deletion mutants and nonsense mutants (with the exception of L1m13, which produces a Cap of only nine amino acids) produced fragments of L1 Cap of the expected sizes, detectable by polyclonal antibodies.

Most of the deletion and nonsense mutants of L1 cap were tested for the presence of the expected L1 Cap N-terminal fragment. Crude protein from transformants was run on a 15% SDS-PAGE, transferred to nitrocellulose, probed with anti-L1 Cap polyclonal antibody, and antigen-antibody complexes were visualized with bacterial alkaline phosphatase-conjugated protein A. L1 was the control Cap from wild-type ScVL1 particles and M was prestained protein markers. Although there appeared to be somewhat lower levels of the L1m15, L1m14, and L1m11 proteins than the equivalent (L1d3) deletion protein, consistent with their inability to interfere, there was not a good correlation between RNA level and protein level. Another construct (pGL1m11d3), with the m11 mutation combined with a deletion of the region of the mRNA encoding amino acids 579–680 of SEQ ID NO:2, interfered as well as d2 (Table 1). Hence the unexpected failure of the nonsense mutants L1m11, L1m14, and L1m15 to interfere was the result of some complex interaction between the 3' portion of the L1 cap mRNA and the nonsense codon, presumably during translation. Both the nonsense mutants and the deletion mutants clearly implicated the amino-terminal portion of L1 Cap, amino acids 1–473 of SEQ ID NO:2, in interference.

EXAMPLE III

Mechanism of interference

The mechanism of interference by overproduction of both Cap and Cap-Pol is thought to be titration of a cellular factor required for viral replication (Valle and Wickner, 1993). Drastic alterations in the ratio of Cap to Cap-Pol are also known to interfere with viral replication (Dinman and Wickner, 1992). Consequently, interference by overproduction of Cap is probably due to distortion of the ratio of Cap to Cap-Pol and is efficient only if the amount of protein synthesized by virtue of the presence of an expression vector is close to that normally produced by the virus in other words, when the viral copy number is low.

However, interference by N-terminal fragments of Cap is insensitive to viral copy number and must therefore take place by a third mechanism. One possibility is negative complementation: the incorporation of one or more copies of a partially functional Cap monomer (an N-terminal fragment) in a nascent viral particle may disrupt the particle. Since there are 118 copies of Cap (and two of Cap-Pol) per particle, if incorporation of a single fragment disrupted a particle, production of N-terminal fragments of Cap would be very efficient in interfering with ScV packaging. N-terminal fragments of the Cap protein of another totivirus are known to be incorporated into aberrant particles (Cadd et al., 1994).

Viral particle preparations were made from a strain without any resident ScV particles (no ScVLa or ScVL1) after introduction of expression vectors producing only the interfering N-terminal fragments of La. Expression of the full-size La Cap resulted in efficient production of empty ScVLa particles, but expression of interfering N-terminal fragments of Cap produced no detectable particles. This result was confirmed by SDS-PAGE of fractions from the gradients.

The same was true of strains producing only the N-terminal fragments of the L1 Cap. However, when two plasmids were introduced—one making the L1 Cap and Cap-Pol proteins and a second making an N-terminal fragment of L1 Cap (L1d2)—the result was the production of empty particles that appeared to have both the fragment and the full-size Cap.

The same particles that apparently had both the full-size Cap and the deletion product were seen when the helper vector produced L1 Cap but not L1 Cap-Pol. This is consistent with the negative complementation model for interference, in which a Cap-Cap interaction is implicated. Only the larger N-terminal fragments of Cap are detected in heteromultimeric viral particles, however. For instance, L1d3 and La1d3 Cap do not appear in viral particles in similar experiments

EXAMPLE IV

Three types of interference were observed with the ScV life cycle due to production of viral proteins from cDNA expression vectors. First, overproduction of both Cap and Cap-Pol, as has been observed previously (Valle and Wickner, 1993), will eliminate ScVL1. This was postulated to involve interaction with cellular proteins. Second, overproduction of Cap alone will cure ScVLa, but not ScVL1. This appears to be due to distortion of the ratio of Cap to Cap-Pol, which is critical (Ribas and Wickner, 1992) and affects ScVLa but not ScVL1 because the copy number of the former is much lower and it is consequently much more sensitive to production of Cap from cDNA clones. Overproduction of L1 Cap is also known to elevate the number of ScVL1 particles per cell (Wickner et al., 1991), making it more difficult to distort the ratio of Cap to Cap-Pol by overexpression of Cap. ScVLa copy number may not be derepressed by overproduction of La Cap. Another totivirus, LRV, can also be cured by overexpression of its capsid polypeptide (Widmer, 1995). Third, and most interesting, is the highly efficient elimination of either ScVL1 or ScVLa by overproduction of N-terminal fragments of their capsid polypeptides. This is a unique method of viral interference.

Interference with ScVLa and ScVL1 by synthesis of fragments of Cap is highly efficient. This interaction might be with either a cellular or viral gene product. If interaction were with some cellular component, this interaction would also be expected to take place with wild-type Cap, which it does not, since curing by wild-type L1 Cap is not detectable and is less efficient with La Cap. Hence, some abnormal interaction must be taking place with some component of the viral particle. There are only three components in the viral particle:

Cap, Cap-Pol, and the viral RNA. These experiments implicate Cap in the fatal interaction.

Production of a complete Cap protein from a nuclear promoter results in formation of empty viral particles. However, fragments of Cap lacking the C-terminus of the protein are not detectably incorporated into viral particles except in the presence of equivalent quantities of wild-type Cap. They appear to be partially crippled in multimer formation. Some N-terminal fragments of Cap appear to be capable of some but not all of the interactions required for particle formation. Recent cryoelectron microscopy has demonstrated that ScVL1 (as well as another fungal dsRNA virus) does have 120 copies of Cap arranged in 12 pentamers (Cheng et al., 1994). The fragments would form heteropentons incapable of correct assembly into particles (e.g., L1d3), or heteromultimeric particles incapable of packaging or replicating the viral RNA (e.g., L1d2).

The region of Cap required for interference includes the region of L1 and La Cap with 37.7% amino acid identity, the only major region of sequence similarity between the two, and its C-terminal border is close to the C-terminal limit of the region with some similarity to the picornavirus vp3 (Bruenn et al., 1989), as shown in FIG. 1. The C-terminal border of the La Cap required for interference maps almost precisely to the end of the region with similarity to vp3 (425–442 compared to 443).

This is consistent with the existence of a similar protein fold (an eightfold beta barrel) in ScV responsible for multimerization.

This very efficient method of interference with viral replication may be useful in other viral systems.

Specifically, it may be readily applicable to making transgenic plants resistant to plant viruses. Many of these are known to have single capsid polypeptides with an eightfold beta barrel structure (Rossmann, 1987) that may also be susceptible to interference by N-terminal capsid polypeptide fragments.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Curing of ScVLa and ScVL1

| | Deletions | | | | |
|---|---|---|---|---|---|
| Construct | aa La cap | Curing (%) | Construct | aa La cap | Curing (%) |
| pGLa4 | 1–697 | 100 | pGLa1m3 | 1–505 | 100 |
| pGLa1 | 1–697 | 100 | pGLa1m4 | 1–442 | 100 |
| pGLa1d1 | 1–502 | 100 | pGLa1m5 | 1–418 | <10 |
| pGLa1d2 | 1–476 | 100 | pGLa1m6 | 1–10 | <10 |
| pGLa1d3 | 1–443 | 100 | | | |
| pGLa1d4 | 1–428 | 50 | | | |
| pGLa1d5 | 1–418 | <10 | | | |
| pGLa1d6 | 1–401 | <10 | | | |
| pGLa1d7 | 6–443 | <10 | | | |
| pGLa1d8 | 98–443 | <10 | | | |

TABLE 1-continued

Curing of ScVLa and ScVL1

| | Deletions | | | | |
|---|---|---|---|---|---|
| Construct | aa L1 cap | Curing (%) | Construct | aa L1 cap | Curing (%) |
| PGL1[a] | 1–680 | 100 | pGL1m15 | 1–500 | <5 |
| pGL1d1 | 1–680 | <5 | pGL1m14 | 1–484 | <5 |
| pGL1d2 | 1–603 | 100 | pGL1m11 | 1–473 | <5 |
| pGL1d3 | 1–476 | 80–100 | pGL1m12 | 1–434 | <5 |
| pGL1d4 | 1–435 | <5 | PGL1m13 | 1–9 | <5 |
| pGL1d5 | 1–433 | <5 | pGL1m11d3 | 1–473 | 100 |

[a]Complete L1 cDNA, producing both Cap and Cap-Pol.

LIST OF REFERENCES CITED

Bordo, D. and Argos, P., *J Mol Biol* 217:721–729 (1991).
Bruenn, J. A. (1988). In "RNA Genetics" (R. D. J. Holland and P. Ahlquist, Eds.), Vol. I, pp. 195–209. CRC Press, Boca Raton, Fla.
Bruenn, J. A. (1993). *Nucleic Acids Res.* 21, 5667–5669.
Bruenn, J., and Kane, W. (1978). *J. Virol.* 26, 762–772.
Bruenn, J. A., et al. (1989). *Nucleic Acids Res.* 17, 7487–7493.
Cadd, T. L., et al. (1994). *J. Virol.* 68, 7738–7745.
Capecchi, M., *Cell* 22:479–488 (1980).
Chelvanayagam, G., et al., *J Mol Biol* 228:220–242 (1992).
Cheng, R. H., et al. (1994). *J. Mol. Biol.* 244, 255–258.
Devereux, J., et al. (1984). *Nucleic Acids Res.* 12, 387–395.
Diamond, M. E., et al. (1989). *J. Virol.* 63, 3983–3990.
Dinman, J. D., and Wickner, R. B. (1992). *J. Virol.* 66, 3669–3678.
Elbe, R. (1992). *Biotechniques* 13, 18–20.
El-Sherbeini, M., et al. (1984). *Mol. Cell. Biol.* 4, 2818–2827.
Fitchen, J. H., and Beachy, R. N. (1993). *Annu. Rev. Microbiol.* 47, 739–763.
French, S. and Robson, B., *J Molecular Evolution* 19:171–175 (1983).
Getzoff, E. D., et al., *Biophys J* 49:191–206 (1986).
Huan, B. -F., et al., (1991). *Proc. Natl. Acad. Sci. USA* 88, 1271–1275.
Klein, T. M., et al., Nature 327:70–73 (1987).
Kunkel, T. A. (1985). *Proc. Natl. Acad. Sci. USA* 82, 488–492.
Lindbo, J. A., and Dougherty, W. G. (1992a). *Mol. Plant-Microbe Interact.* 5, 144–153.
Lindbo, J. A., and Dougherty, W. G. (1992b). *Virology* 189, 725–733.
Mannino, R. J. and Gould-Fogerite, S., *BioTechniques* 6:682–690 (1988).
Miller, L. K., *Bioessays* 11:91–95 (1989).
Park, C. -M., et al., *Virology* 216:451–454 (1996).
Reilly, J. D., et al. (1984). *Biochem. Biophys. Res. Commun.* 121, 619–625.
Ribas, J. C., and Wickner, R. B. (1992). *Proc. Natl. Acad. Sci. USA* 89, 2185–2189.
Rossmann, M. (1987). *Bioessays* 7, 99–103.
Sambrook, J., et al. (1989). "Molecular Cloning: A Laboratory Manual," 2nd ed. Cold Spring Harbor Laboratory Press, Cold Spring Harbor, N.Y.
Schena, M., et al. (1991). *Methods Enzymol.* 194, 389–398.
Shen, Y., and Bruenn, J. A. (1993). *Virology* 195, 481–491.
Shigekawa, K. and Dower, W. J., *BioTechniques* 6:742–751 (1988).

Taylor, W. R., *J Theor Biol* 119:205–218 (1986).
Thiele, D. J., et al. (1984). *Mol. Cell. Biol.* 4, 92–100.
Tu, C. -L., et al. (1992). *Proc. Natl. Acad. Sci. USA* 89, 8636–8640.
Tzeng, T. -H., et al. (1992). *J. Virol.* 66, 999–1006.

Valle, R. P., and Wickner, R. B. (1993) *J. Virol.* 67, 2764–2771.
Wickner, R. B., et al. (1991). *J. Virol.* 65, 155–161.
Widmer, G. (1995). *J. Virol.* 69, 4122–4126.
Yao, W., et al. (1995). *J. Virol.* 69, 1917–1919.

What is claimed is:

1. A viral capsid polypeptide capable of inhibiting viral packaging, said viral capsid polypeptide having an amino acid sequence selected from the group consisting of amino acids 1 to 473 of SEQ ID NO:2 and amino acids 1 to 443 of SEQ ID NO:4.

2. The viral capsid polypeptide capable of inhabiting viral packaging, said viral capsid polypeptide having an amino acid sequence selected from the group consisting of amino acids 1 to 443 of SEQ ID NO:4.

3. The viral capsid polypeptide of claim 1 wherein said viral capsid polypeptide is encoded by nucleotides 24 to 1352 of SEQ ID NO:3.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 4580 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GAAAAATTTT  TAAATTCATA  TAACTCCCCA  TGCTAAGATT  TGTTACTAAA  AACTCTCAAG    60
ATAAATCGTC  TGATCTATTC  TCTATTTGTT  CTGATCGCGG  AACTTTTGTT  GCTCATAATA   120
GAGTTCGGAC  TGATTTCAAG  TTTGACAACT  TAGTATTTAA  CCGAGTTTAT  GGTGTTTCTC   180
AAAAATTTAC  GTTAGTCGGT  AACCCGACAG  TCTGCTTTAA  TGAAGGCAGT  TCTTACCTAG   240
AAGGTATTGC  TAAAAAGTAC  CTAACTTTGG  ATGGAGGACT  TGCCATTGAC  AATGTCCTCA   300
ATGAGTTGAG  ATCCACTTGC  GGTATCCCAG  GTAATGCTGT  TGCGTCTCAT  GCGTATAATA   360
TTACATCCTG  GCGTTGGTAT  GACAATCACG  TGGCACTGTT  GATGAACATG  TTGCGTGCTT   420
ACCACTTACA  AGTATTGACC  GAACAGGGCC  AATATAGCGC  TGGAGATATC  CCTATGTACC   480
ATGATGGACA  TGTCAAAATC  AAGCTACCAG  TGACTATCGA  TGACACGGCA  GGCCCAACAC   540
AATTCGCTTG  GCCTAGTGAC  AGGTCTACTG  ATTCGTATCC  TGATTGGGCA  CAGTTTTCTG   600
AATCATTTCC  ATCAATCGAC  GTCCCGTACC  TAGATGTTAG  GCCATTGACC  GTAACGGAAG   660
TCAATTTCGT  GCTTATGATG  ATGAGTAAGT  GGCATAGACG  TACTAACTTA  GCGATAGACT   720
ACGAGGCACC  CCAACTAGCT  GATAAGTTCG  CTTACCGCCA  TGCGCTTACT  GTTCAAGACG   780
CTGACGAGTG  GATAGAAGGC  GATAGAACTG  ATGACCAGTT  CCGCCCCCCC  TCGTCTAAAG   840
TAATGTTATC  GGCACTTCGT  AAGTACGTGA  ACCGTAACAG  GCTGTACAAT  CAGTTTTACA   900
CTGCAGCACA  ACTGTTAGCT  CAAATTATGA  TGAAACCTGT  CCCTAACTGC  GCTGAGGGCT   960
ACGCTTGGCT  GATGCATGAC  GCATTGGTCA  ATATACCAAA  ATTTGGGTCT  ATTCGAGGAA  1020
GGTACCCTTT  TTTGTTATCA  GGTGATGCAG  CGTTGATTCA  GGCTACAGCC  CTAGAAGACT  1080
GGTCTGCTAT  CATGGCGAAA  CCCGAGCTGG  TGTTCACTTA  CGCGATGCAG  GTGTCAGTAG  1140
CGTTAAACAC  CGGACTATAC  TTACGTCGCG  TTAAGAAAAC  AGGCTTCGGC  ACAACTATAG  1200
ATGACAGCTA  TGAAGATGGA  GCGTTTTTGC  AACCGGAGAC  GTTCGTTCAG  GCCGCACTAG  1260
CATGTTGTAC  CGGACAAGAT  GCGCCCCTAA  ATGGGATGTC  AGATGTGTAT  GTCACTTATC  1320
CAGATCTTCT  AGAATTTGAT  GCTGTTACAC  AAGTACCCAT  CACGGTCATT  GAGCCCGCTG  1380
GCTATAACAT  TGTTGATGAT  CATTTAGTGG  TTGTGGGTGT  ACCTGTGGCA  TGTTCACCAT  1440
ACATGATATT  TCCAGTAGCT  GCGTTTGATA  CTGCAAATCC  TTACTGTGGG  AATTTTGTCA  1500
TTAAGGCTGC  TAACAAGTAT  CTCCGTAAGG  GTGCCGTGTA  TGATAAACTC  GAAGCATGGA  1560
AGTTGGCCTG  GGCACTGAGG  GTAGCCGGGT  ATGACACTCA  CTTCAAAGTG  CATGGCGATA  1620
```

```
CACACGGCTT  AACTAAGTTC  TATGCTGACA  ACAGTGACAC  ATGGACACAC  ATACCTGAAT   1680
TTGTCACTGA  CGGTGACGTG  ATGGAAGTAT  TCGTTACTGC  CATCGAACGC  AGAGCTAGAC   1740
ATTTCGTTGA  ACTACCTAGA  CTGAATTCAC  CAGCATTCTT  CAGATCTGTA  GAAGTCAGCA   1800
CCACTATATA  TGATACTCAT  GTGCAGGCTG  GTGCGCATTC  AGTGTATCAT  GCTAGACGAA   1860
TCAATCTTGA  TTATGTTAAG  CCTGTTTCGA  CCGGCATTCA  GGTGATCAAT  GCGGGCGAAC   1920
TTAAGAACTA  CTGGGGTAGT  GTGCGTCGTA  CTCAGCAGGG  TTTAGGAGTG  GTAGGTCTTA   1980
CGATGCCAGC  TGTAATGCCT  ACCGGAGAAC  CTACAGCTGG  CGCTGCCCAC  GAAGAGTTGA   2040
TAGAACAGGC  GGACAATGTT  TTAGTAGAGT  AAACGTAATC  GAACCCTCAC  ACGGACCCCG   2100
CCCTACAAGG  TACATACTGC  AGGAACCAGG  TACGTACCCT  GCGTGGATTA  GATTCAGGAA   2160
CAGAGTACAA  GCTGTATCGC  GTCAGAAAGC  CACTCACTTC  TTGTTTGACA  TCGTACCTGC   2220
CGCAGTAATT  AGTGATTTTA  CTACGTCTGA  CACGTCTTCG  TTTGCATACA  AATCGCACAC   2280
CTACGCTGCA  AATGTAACAG  CATTGAGGTT  CAGTGACACT  TATGCCTTGT  ACGTACAGAC   2340
TGATACCAAT  ATGACAATTT  TAAGCCCAGC  GGCGCGTCGC  CAGGCTTCTG  CGACGTACTC   2400
ACAGGTGGCA  GGGTTTTGTT  ATAACACACC  TACCGTTATG  GATTCGCTAG  CGAATATCTT   2460
GGACGTAGAC  CGCAATATAC  GACCCAAACA  CTTCAAGGGT  TTACGGCTAT  ACACCAGCTC   2520
TAAGGTCACT  GCTCAACATC  ATACTCACTT  GCGGCCAGAC  GAGCTAGTGG  AAGCGGCCGC   2580
AAAGGTCTCG  CCTAGACGTA  AATACTACCT  AATGTGTGTA  GTTGAGCTGC  TCGCGAACTT   2640
ACAAGTAGAT  CTTGAAGCAG  CAGTAGCTAC  TATTCTAGCA  TATGTCCTGA  CACTAAGTGA   2700
AAAATTTGTA  CCAATTTTCT  TGGATTCTAG  AGCAATATGG  GTCGGTGAGC  CTGGGCCTGA   2760
TGCTCTGACT  GCACGTCTCA  AGGCCAGTAG  TGGGCAGATC  AAGAGCATAC  ACACGGCTGA   2820
TTACGAACCA  CTCACTGAAC  TATTCGAGTT  AGCAGTATTG  ATGAACCGAG  GTGTTGGCCA   2880
TGTCTCTTGG  CAAGCTGAAA  AGGATCATCG  CTTGAATCCC  GACGTGGCTG  TAGTTGATCA   2940
AGCACGGCTA  TATTCGTGTG  TGCGCGACAT  GTTCGAAGGA  TCAAAGCAGA  CGTATAAATA   3000
TCCCTTTATG  ACGTGGGATG  ACTACACTGC  AAACAGATGG  GAGTGGGTTC  CAGGTGGCAG   3060
TGTCCACTCT  CAATACGAAG  AAGACAACGA  TTATATCTAT  CCTGGTCAGT  ATACTAGGAA   3120
CAAGTTCATA  ACTGTTAACA  AAATGCCCAA  ACACAAAATA  TCTAGAATGA  TAGCATCACC   3180
GCCTGAGGTA  CGAGCTTGGA  CGTCGACGAA  GTACGAATGG  GGCAAGCAAC  GTGCTATCTA   3240
CGGGACGGAT  CTACGAAGTA  CACTGATAAC  TAACTTTGCA  ATGTTCAGGT  GCGAGGATGT   3300
TCTCACTCAC  AAGTTCCCAG  TAGGCGACCA  GGCAGAGGCA  GCAAAGGTGC  ACAAACGGGT   3360
GAACATGATG  CTGGACGGTG  CCTCTAGTTT  CTGCTTCGAT  TATGATGACT  TCAATTCTCA   3420
GCATTCGATA  GCTAGTATGT  ATACGGTTTT  GTGCGCTTTC  AGGGACACAT  TTAGTCGCAA   3480
CATGTCTGAT  GAACAAGCAG  AGGCGATGAA  CTGGGTGTGT  GAGTCCGTCA  GACACATGTG   3540
GGTACTAGAT  CCTGATACCA  AGGAGTGGTA  CAGACTACAA  GGTACATTAC  TGTCAGGATG   3600
GCGGTTAACC  ACATTTATGA  ATACTGTGCT  AAACTGGGCG  TATATGAAAT  TAGCTGGCGT   3660
ATTTGATCTG  GATGACGTTC  AAGACTCGGT  ACACAACGGT  GATGATGTTA  TGATTAGTCT   3720
CAACCGCGTG  AGCACAGCAG  TGAGAATAAT  GGACGCTATG  CACCGGATAA  ATGCGCGAGC   3780
ACAGCCGGCG  AAGTGTAACT  TGTTTTCGAT  AAGTGAATTT  CTGAGGGTAG  AACACGGTAT   3840
GAGCGGAGGC  GATGGTCTTG  GGGCTCAGTA  CTTAAGTAGG  TCTTGTGCTA  CTCTTGTACA   3900
CAGTAGGATT  GAGTCTAACG  AACCACTGTC  AGTAGTACGA  GTTATGGAAG  CAGACCAGGC   3960
TAGATTGCGC  GACCTGGCAA  ACAGAACGCG  GGTACAATCT  GCGGTAACAG  CGATAAAAGA   4020
```

```
ACAACTCGAC  AAACGTGTCA  CTAAGATATT  CGGAGTTGGT  GATGACGTTG  TGCGCGACAT    4080

ACACACAGCT  CACAGGGTGT  GTGGCGGTAT  CTCGACTGAT  ACCTGGGCAC  CGGTTGAAAC    4140

TAAGATAATA  ACAGACAATG  AAGCATATGA  AATACCATAC  GAAATAGATG  ATCCATCATT    4200

TTGGCCAGGG  GTAAATGATT  ATGCTTATAA  AGTCTGGAAA  AATTTCGGAG  AACGACTCGA    4260

ATTTAATAAA  ATTAAAGATG  CCGTAGCTAG  AGGGAGTAGG  AGCACTATAG  CTCTGAAACG    4320

TAAGGCTAGG  ATAACATCTG  AGAAGAATGA  ATTCGCTAAC  AAGTCGGAAT  GGGAAAGGAC    4380

AATGTACAAA  GCCTATAAGG  GTTTGGCAGT  CTCATACTAT  GCTAACCTGA  GCAAATTCAT    4440

GAGTATACCA  CCAATGGCGA  ACATTGAATT  TGGGCAGGCT  AGATATGCTA  TGCAAGCAGC    4500

CCTTGATAGT  TCTGATCCAC  TCCGGGCATT  ACAGGTCATA  CTGTAGTTGC  CAAAAAGATA    4560

ATGGGAATTA  CCCATATGCA                                                   4580
```

(2) INFORMATION FOR SEQ ID NO:2:

(i) SEQUENCE CHARACTERISTICS:
        (A) LENGTH: 680 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

```
Met  Leu  Arg  Phe  Val  Thr  Lys  Asn  Ser  Gln  Asp  Lys  Ser  Ser  Asp  Leu
 1              5                       10                      15

Phe  Ser  Ile  Cys  Ser  Asp  Arg  Gly  Thr  Phe  Val  Ala  His  Asn  Arg  Val
              20                       25                      30

Arg  Thr  Asp  Phe  Lys  Phe  Asp  Asn  Leu  Val  Phe  Asn  Arg  Val  Tyr  Gly
         35                      40                      45

Val  Ser  Gln  Lys  Phe  Thr  Leu  Val  Gly  Asn  Pro  Thr  Val  Cys  Phe  Asn
     50                       55                      60

Glu  Gly  Ser  Ser  Tyr  Leu  Glu  Gly  Ile  Ala  Lys  Lys  Tyr  Leu  Thr  Leu
 65                      70                      75                      80

Asp  Gly  Gly  Leu  Ala  Ile  Asp  Asn  Val  Leu  Asn  Glu  Leu  Arg  Ser  Thr
                     85                      90                      95

Cys  Gly  Ile  Pro  Gly  Asn  Ala  Val  Ala  Ser  His  Ala  Tyr  Asn  Ile  Thr
                100                     105                     110

Ser  Trp  Arg  Trp  Tyr  Asp  Asn  His  Val  Ala  Leu  Leu  Met  Asn  Met  Leu
              115                     120                     125

Arg  Ala  Tyr  His  Leu  Gln  Val  Leu  Thr  Glu  Gln  Gly  Gln  Tyr  Ser  Ala
         130                     135                     140

Gly  Asp  Ile  Pro  Met  Tyr  His  Asp  Gly  His  Val  Lys  Ile  Lys  Leu  Pro
145                      150                     155                     160

Val  Thr  Ile  Asp  Asp  Thr  Ala  Gly  Pro  Thr  Gln  Phe  Ala  Trp  Pro  Ser
                     165                     170                     175

Asp  Arg  Ser  Thr  Asp  Ser  Tyr  Pro  Asp  Trp  Ala  Gln  Phe  Ser  Glu  Ser
                180                     185                     190

Phe  Pro  Ser  Ile  Asp  Val  Pro  Tyr  Leu  Asp  Val  Arg  Pro  Leu  Thr  Val
              195                     200                     205

Thr  Glu  Val  Asn  Phe  Val  Leu  Met  Met  Met  Ser  Lys  Trp  His  Arg  Arg
         210                     215                     220

Thr  Asn  Leu  Ala  Ile  Asp  Tyr  Glu  Ala  Pro  Gln  Leu  Ala  Asp  Lys  Phe
225                      230                     235                     240

Ala  Tyr  Arg  His  Ala  Leu  Thr  Val  Gln  Asp  Ala  Asp  Glu  Trp  Ile  Glu
```

-continued

|     |     |     |     | 245 |     |     |     | 250 |     |     |     | 255 |     |     |
| --- | --- | --- | --- | --- | --- | --- | --- | --- | --- | --- | --- | --- | --- | --- |
| Gly | Asp | Arg | Thr 260 | Asp | Asp | Gln | Phe 265 | Arg | Pro | Pro | Ser | Ser 270 | Lys | Val | Met |
| Leu | Ser | Ala 275 | Leu | Arg | Lys | Tyr | Val 280 | Asn | Arg | Asn | Arg 285 | Leu | Tyr | Asn | Gln |
| Phe | Tyr 290 | Thr | Ala | Ala | Gln 295 | Leu | Leu | Ala | Gln | Ile 300 | Met | Met | Lys | Pro | Val |
| Pro 305 | Asn | Cys | Ala | Glu 310 | Gly | Tyr | Ala | Trp | Leu 315 | Met | His | Asp | Ala | Leu 320 | Val |
| Asn | Ile | Pro | Lys | Phe 325 | Gly | Ser | Ile | Arg | Gly 330 | Arg | Tyr | Pro | Phe | Leu 335 | Leu |
| Ser | Gly | Asp | Ala 340 | Ala | Leu | Ile | Gln | Ala 345 | Thr | Ala | Leu | Glu | Asp 350 | Trp | Ser |
| Ala | Ile | Met 355 | Ala | Lys | Pro | Glu | Leu 360 | Val | Phe | Thr | Tyr | Ala 365 | Met | Gln | Val |
| Ser | Val 370 | Ala | Leu | Asn | Thr | Gly 375 | Leu | Tyr | Leu | Arg | Arg 380 | Val | Lys | Lys | Thr |
| Gly 385 | Phe | Gly | Thr | Thr | Ile 390 | Asp | Asp | Ser | Tyr | Glu 395 | Asp | Gly | Ala | Phe | Leu 400 |
| Gln | Pro | Glu | Thr | Phe 405 | Val | Gln | Ala | Ala | Leu 410 | Ala | Cys | Cys | Thr | Gly 415 | Gln |
| Asp | Ala | Pro | Leu 420 | Asn | Gly | Met | Ser | Asp 425 | Val | Tyr | Val | Thr | Tyr 430 | Pro | Asp |
| Leu | Leu | Glu 435 | Phe | Asp | Ala | Val | Thr 440 | Gln | Val | Pro | Ile | Thr 445 | Val | Ile | Glu |
| Pro | Ala | Gly 450 | Tyr | Asn | Ile | Val 455 | Asp | Asp | His | Leu | Val 460 | Val | Val | Gly | Val |
| Pro 465 | Val | Ala | Cys | Ser | Pro 470 | Tyr | Met | Ile | Phe | Pro 475 | Val | Ala | Ala | Phe | Asp 480 |
| Thr | Ala | Asn | Pro | Tyr 485 | Cys | Gly | Asn | Phe | Val 490 | Ile | Lys | Ala | Ala | Asn 495 | Lys |
| Tyr | Leu | Arg | Lys 500 | Gly | Ala | Val | Tyr | Asp 505 | Lys | Leu | Glu | Ala | Trp 510 | Lys | Leu |
| Ala | Trp | Ala 515 | Leu | Arg | Val | Ala | Gly 520 | Tyr | Asp | Thr | His | Phe 525 | Lys | Val | His |
| Gly | Asp 530 | Thr | His | Gly | Leu | Thr 535 | Lys | Phe | Tyr | Ala | Asp 540 | Asn | Ser | Asp | Thr |
| Trp 545 | Thr | His | Ile | Pro | Glu 550 | Phe | Val | Thr | Asp | Gly 555 | Asp | Val | Met | Glu | Val 560 |
| Phe | Val | Thr | Ala | Ile 565 | Glu | Arg | Arg | Ala | Arg 570 | His | Phe | Val | Glu | Leu 575 | Pro |
| Arg | Leu | Asn | Ser 580 | Pro | Ala | Phe | Phe | Arg 585 | Ser | Val | Glu | Val | Ser 590 | Thr | Thr |
| Ile | Tyr | Asp 595 | Thr | His | Val | Gln | Ala 600 | Gly | Ala | His | Ser | Val 605 | Tyr | His | Ala |
| Arg | Arg 610 | Ile | Asn | Leu | Asp | Tyr 615 | Val | Lys | Pro | Val | Ser 620 | Thr | Gly | Ile | Gln |
| Val 625 | Ile | Asn | Ala | Gly | Glu 630 | Leu | Lys | Asn | Tyr | Trp 635 | Gly | Ser | Val | Arg | Arg 640 |
| Thr | Gln | Gln | Gly | Leu 645 | Gly | Val | Val | Gly | Leu 650 | Thr | Met | Pro | Ala | Val 655 | Met |
| Pro | Thr | Gly | Glu 660 | Pro | Thr | Ala | Gly | Ala 665 | Ala | His | Glu | Glu | Leu 670 | Ile | Glu |

Gln Ala Asp Asn Val Leu Val Glu
675 680

( 2 ) INFORMATION FOR SEQ ID NO:3:

( i ) SEQUENCE CHARACTERISTICS:
( A ) LENGTH: 4615 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| GAATTTTTCG | GTGAACCGGA | ATTATGTCGT | CTCTGTTAAA | TTCATTACTA | CCAGAATATT | 60 |
| TTAAACCTAA | AACTAATTTG | AATATCAACT | CTTCTAGGGT | CCAATATGGC | TTTAATGCTC | 120 |
| GCATTGATAT | GCAGTATGAA | GACGATAGTG | GGACTAGAAA | AGGCTCAAGA | CCCAATGCAT | 180 |
| TTATGTCTAA | CACAGTTGCT | TTTATAGGAA | ACTATGAAGG | TATTATTGTT | GATGACATTC | 240 |
| CGATATTGGA | TGGTCTTAGG | GCCGACATTT | TTGATACTCA | TGGTGACTTA | GACATGGGCC | 300 |
| TCGTTGAGGA | TGCATTGTCT | AAGAGTACCA | TGATTAGAAG | GAATGTACCA | ACTTATACTG | 360 |
| CTTACGCGAG | TGAATTACTG | TATAAGAGAA | ACCTTACATC | TCTATTTTAC | AATATGCTCC | 420 |
| GTTTATACTA | CATTAAAAAA | TGGGGCAGTA | TTAAGTATGA | AAAAGATGCC | ATCTTTTATG | 480 |
| ATAATGGCCA | CGCCTGTCTT | TTAAACAGGC | AATTGTTTCC | AAAGTCTCGT | GATGCTTCTT | 540 |
| TGGAATCAAG | CCTCTCTTTG | CCTGAGGCTG | AAATTGCAAT | GCTTGATCCT | GGCCTGGAAT | 600 |
| TTCCAGAAGA | GGATGTGCCT | GCAATTTTAT | GGCACGGCAG | AGTGTCATCC | AGAGCAACGT | 660 |
| GTATCTTAGG | GCAAGCTTGC | TCAGAGTTCG | CGCCTCTGGC | CCCCTTTTCG | ATTGCGCATT | 720 |
| ATTCACCACA | ATTGACGAGA | AAACTATTTG | TCAATGCGCC | CGCTGGGATT | GAGCCTAGCT | 780 |
| CCGGGCGGTA | TACTCACGAG | GATGTAAAAG | ATGCGATTAC | GATCCTTGTG | TCTGCAAACC | 840 |
| AGGCTTATAC | TGACTTTGAA | GCAGCATACT | TGATGCTTGC | TCAAACGTTG | GTCTCACCTG | 900 |
| TACCACGCAC | TGCCGAAGCA | AGTGCATGGT | TCATCAATGC | TGGCATGGTC | AATATGCCAA | 960 |
| CTTTGTCATG | TGCAAATGGT | TATTATCCAG | CACTGACCAA | TGTCAATCCT | TACCACCGGC | 1020 |
| TAGACACATG | GAAAGATACG | TTAAATCATT | GGGTGGCTTA | TCCCGACATG | CTGTTTTACC | 1080 |
| ATTCAGTGGC | AATGATTGAG | AGCTGCTATG | TTGAACTCGG | GAATGTGGCT | CGTGTGTCAG | 1140 |
| ACAGTGATGC | AATAAACAAA | TACACTTTCA | CTGAGCTATC | AGTGCAAGGA | CGGCCTGTTA | 1200 |
| TGAATCGAGG | AATTATTGTA | GATCTGACAC | TTGTGGCAAT | GCGTACTGGT | AGGGAGATCT | 1260 |
| CACTACCTTA | CCCGGTCAGC | TGTGGCCTGA | CCCGTACAGA | CGCGTTATTG | CAAGGTACTG | 1320 |
| AGATTCACGT | TCCAGTTGTT | GTCAAAGATA | TCGACATGCC | CCAGTATTAC | AACGCGATTG | 1380 |
| ATAAGGATGT | TATTGAGGGG | CAGGAAACTG | TGATTAAAGT | GAAACAGCTG | CCACCAGCTA | 1440 |
| TGTATCCAAT | TTATACTTAC | GGGATCAACA | CTACTGAATT | CTATTCTGAC | CATTTTGAAG | 1500 |
| ACCAGGTACA | AGTTGAAATG | GCACCAATCG | ATAATGGAAA | AGCAGTTTTT | AACGATGCAA | 1560 |
| GAAAGTTTTC | GAAATTTATG | TCCATAATGC | GCATGATGGG | GAATGATGTT | ACTGCTACTG | 1620 |
| ATTTAGTTAC | AGGTAGAAAA | GTGTCGAATT | GGGCCGACAA | CTCATCAGGG | CGTTTCTTGT | 1680 |
| ACACGGATGT | GAAGTATGAA | GGACAAACTG | CCTTTTTGGT | TGATATGGAT | ACTGTCAAGG | 1740 |
| CGAGAGACCA | CTGTTGGGTG | TCAATTGTTG | ATCCTAATGG | TACAATGAAC | TTGTCATATA | 1800 |
| AGATGACCAA | TTTTAGAGCA | GCAATGTTTT | CTAGAAACAA | GCCCTTGTAT | ATGACAGGGG | 1860 |
| GGTCAGTCAG | GACCATAGCT | ACTGGCAATT | ATCGAGATGC | TGCTGAAAGA | TTACGTGCAA | 1920 |

| | | | | | | |
|---|---|---|---|---|---|---|
| TGGATGAAAC | GCTCAGATTA | AAACCTTTTA | AGATTACTGA | GAAGTTGGAT | TTTCGTGTAG | 1980 |
| CAGCTTACGC | GATACCAAGT | TTGTCGGGCA | GCAATATGCC | ATCCTTACAC | CATCAGGAAC | 2040 |
| AACTACAGAT | ATCAGAAGTG | GACGCGGAAC | CAATCAATCC | TATAGGAGAG | GACGAACTTC | 2100 |
| CACCGGATAT | AGAATAGGTG | TCGAAGACGA | TGAGGACTTA | GATATTGGTA | CGGTCAAATA | 2160 |
| CATTGTGCCA | TTGTATTTGA | ACGGTGATAA | TGTGGCACAA | AATTGTTTAG | AAGCAACACA | 2220 |
| CGTGCTTATC | AAAGCTTGTA | GTATTGCGAA | CCGGATTGTA | GATGACGGAG | AGGGTCACTG | 2280 |
| TTTCACACAG | CAAGGGCTGG | CGCAGCAGTG | GATCTTCCAT | AGGGGGGAGA | TGATATTTGT | 2340 |
| GAAGGCGGTA | CGCATTGGTC | AACTCAATGC | ATATTATGTA | GACTATAAGA | ACGTCACAAA | 2400 |
| TTATAGTCTT | AAAACCGCTG | CTCAAGTAGG | AGCGACGATA | TCAAATAACT | TACGCCACGG | 2460 |
| ATTTGTTGAC | AATCAACAAG | ACGCATACAC | GCGCTTGGTT | GCCAACTACT | CTGATACGCG | 2520 |
| GAAGTGGATA | CGTGACAATT | TTACATATAA | TTATAATATG | GAGAAAGAAA | AGTATAGGAT | 2580 |
| AACCCAATAC | CACCATACAC | ATGTGAGGTT | GAAAGATTTG | TTTCCATCCA | GGAAAATAGT | 2640 |
| TAAACTAGAG | GGATATGAAG | CCTTGTTGGC | AATGATGCTA | GACAGGTTTA | ACAACATAGA | 2700 |
| GTCAACACAT | GTAACTTTCT | TCACATATTT | AAGAGCACTA | CCTGACCGTG | AAAAAGAAGT | 2760 |
| CTTTATTAGC | TTAGTCTTAA | ACTATAATGG | CCTTGGCAGA | GAGTGGTTGA | AGTCTGAAGG | 2820 |
| TGTTAGGGCT | AAACAAGCAC | AAGGTACTGT | GAAATACGAT | ATGAGTAAAC | TATTTGAACT | 2880 |
| GAATGTACTA | GAGAACGGAG | TTGACGAAGA | AGTTGACTGG | GAGAAAGAGA | AACGCAACAG | 2940 |
| GTCAGATATC | AAGACTGTTA | ACATAAGTTA | TGCAAAAGTT | CTCGAACATT | GTAGAGAGCT | 3000 |
| ATTCATCATG | GCGAGGGCCG | AAGGGAAACG | GCCAATGAGG | ATGAAATGGC | AAGAGTACTG | 3060 |
| GAGGCAGAGA | GCAGTTATCA | TGCCAGGTGG | ATCGGTCCAC | AGTCAACATC | CAGTCGAACA | 3120 |
| GGACGTGATT | AGAGTATTAC | CCAGAGAAAT | CAGAAGTAAG | AAGGGGGTGG | CAAGTGTCAT | 3180 |
| GCCATACAAA | GAACAGAAGT | ATTTCACGTC | CAGAAGGCCG | GAAATACACG | CTTACACTTC | 3240 |
| AACGAAATAC | GAGTGGGGAA | AAGTGAGGGC | ACTATATGGG | TGTGATTTTT | CATCACATAC | 3300 |
| AATGGCTGAT | TTTGGATTGT | TACAATGCGA | GGATACATTC | CCGGGCTTTG | TACCAACAGG | 3360 |
| GTCTTACGCC | AATGAGGATT | ATGTCAGGAC | CAGAATTGCT | GGGACTCACT | CATTGATCCC | 3420 |
| TTTCTGTTAC | GATTTCGATG | ATTTCAACAG | CCAACATTCA | AAGGAAGCCA | TGCAAGCAGT | 3480 |
| GATTGATGCA | TGGATATCTG | TCTATCACGA | TAAGTTAACA | GATGACCAGA | TAGAGGCGGC | 3540 |
| AAAGTGGACA | CGAAACTCGG | TAGATAGAAT | GGTCGCTCAC | CAACCTAACA | CTGGTGAGAC | 3600 |
| TTATGATGTT | AAAGGGACAC | TGTTTAGTGG | CTGGCGATTA | ACAACATTTT | TCAATACGGC | 3660 |
| GTTGAACTAT | TGCTACCTGG | CTAATGCAGG | TATAAACTCA | CTAGTGCCAA | CGAGTCTCCA | 3720 |
| TAATGGTGAT | GATGTTTTTG | CAGGGATAAG | GACAATAGCT | GACGGTATTT | CTTTGATCAA | 3780 |
| AAACGCCGCA | GCCACGGGAG | TTCGCGCTAA | TACAACTAAA | ATGAACATTG | GTACGATAGC | 3840 |
| AGAGTTTTTG | AGAGTTGATA | TGCGTGCAAA | AAATAGTACT | GGCAGTCAGT | ATTTAACAAG | 3900 |
| AGGGATTGCT | ACCTTCACGC | ACAGTAGGGT | TGAGTCTGAT | GCACCACTGA | CATTGCGCAA | 3960 |
| TCTAGTATCT | GCTTACAAAA | CCAGATATGA | CGAGATTTTA | GCTCGTGGCG | CAAGCATCGA | 4020 |
| TAACATGAAG | CCACTCTATC | GTAAGCAATT | ATTTTTTGCT | AGAAAGTTGT | TCAATGTCGA | 4080 |
| GAAGGACATT | GTTGACAATC | TGATAACGAT | GGACATATCA | TGTGGCGGTT | TGCAAGAAAA | 4140 |
| GGGTAGGGTA | TCAGAGATGG | TGTTACAGGA | GGTTGACATT | GAGAATATAG | ATAGTTATAG | 4200 |
| GAAGACAAGG | ATGATCGCCA | AACTGATTGA | CAAGGGGGTT | GGCGATTATA | CTGCATTCCT | 4260 |
| GAAAACTAAC | TTTTCCGAGA | TAGCTGATGC | TATCACAAGA | GAGACACGTG | TAGAGTCAGT | 4320 |

-continued

```
GACCAAGGCT  TATAATGTTA  AGAAGAAAAC  GGTCGTACGC  GCGTTTAGGG  ACCTAAGCGC    4380

AGCATATCAT  GAAAGAGCGG  TGAGACATGC  TTGGAAGGGG  ATGAGTGGAC  TACACATAGT    4440

CAACAGGATT  CGTATGGGAG  TGAGCAACTT  AGTAATGGTT  GTTAGCAAAA  TCAATCCTGC    4500

AAAAGCTAAT  GTGCTAGCCA  AATCAGGAGA  TCCTACAAAA  TGGCTTGCAG  TCCTTACATG    4560

ATATACAGGC  AACCACATAA  GACCTGAGAA  CAAAGAGTAC  ATACGATACT  ACGCA         4615
```

( 2 ) INFORMATION FOR SEQ ID NO:4:

( i ) SEQUENCE CHARACTERISTICS:
        ( A ) LENGTH: 697 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:4:

```
Met  Ser  Ser  Leu  Leu  Asn  Ser  Leu  Leu  Pro  Glu  Tyr  Phe  Lys  Pro  Lys
 1              5                             10                            15

Thr  Asn  Leu  Asn  Ile  Asn  Ser  Ser  Arg  Val  Gln  Tyr  Gly  Phe  Asn  Ala
              20                       25                       30

Arg  Ile  Asp  Met  Gln  Tyr  Glu  Asp  Asp  Ser  Gly  Thr  Arg  Lys  Gly  Ser
         35                       40                       45

Arg  Pro  Asn  Ala  Phe  Met  Ser  Asn  Thr  Val  Ala  Phe  Ile  Gly  Asn  Tyr
     50                       55                       60

Glu  Gly  Ile  Ile  Val  Asp  Asp  Ile  Pro  Ile  Leu  Asp  Gly  Leu  Arg  Ala
65                       70                       75                       80

Asp  Ile  Phe  Asp  Thr  His  Gly  Asp  Leu  Asp  Met  Gly  Leu  Val  Glu  Asp
                    85                       90                       95

Ala  Leu  Ser  Lys  Ser  Thr  Met  Ile  Arg  Arg  Asn  Val  Pro  Thr  Tyr  Thr
              100                     105                     110

Ala  Tyr  Ala  Ser  Glu  Leu  Leu  Tyr  Lys  Arg  Asn  Leu  Thr  Ser  Leu  Phe
         115                     120                     125

Tyr  Asn  Met  Leu  Arg  Leu  Tyr  Tyr  Ile  Lys  Lys  Trp  Gly  Ser  Ile  Lys
     130                     135                     140

Tyr  Glu  Lys  Asp  Ala  Ile  Phe  Tyr  Asp  Asn  Gly  His  Ala  Cys  Leu  Leu
145                     150                     155                     160

Asn  Arg  Gln  Leu  Phe  Pro  Lys  Ser  Arg  Asp  Ala  Ser  Leu  Glu  Ser  Ser
                    165                     170                     175

Leu  Ser  Leu  Pro  Glu  Ala  Glu  Ile  Ala  Met  Leu  Asp  Pro  Gly  Leu  Glu
              180                     185                     190

Phe  Pro  Glu  Glu  Asp  Val  Pro  Ala  Ile  Leu  Trp  His  Gly  Arg  Val  Ser
         195                     200                     205

Ser  Arg  Ala  Thr  Cys  Ile  Leu  Gly  Gln  Ala  Cys  Ser  Glu  Phe  Ala  Pro
     210                     215                     220

Leu  Ala  Pro  Phe  Ser  Ile  Ala  His  Tyr  Ser  Pro  Gln  Leu  Thr  Arg  Lys
225                     230                     235                     240

Leu  Phe  Val  Asn  Ala  Pro  Ala  Gly  Ile  Glu  Pro  Ser  Ser  Gly  Arg  Tyr
                    245                     250                     255

Thr  His  Glu  Asp  Val  Lys  Asp  Ala  Ile  Thr  Ile  Leu  Val  Ser  Ala  Asn
              260                     265                     270

Gln  Ala  Tyr  Thr  Asp  Phe  Glu  Ala  Ala  Tyr  Leu  Met  Leu  Ala  Gln  Thr
         275                     280                     285

Leu  Val  Ser  Pro  Val  Pro  Arg  Thr  Ala  Glu  Ala  Ser  Ala  Trp  Phe  Ile
              290                     295                     300
```

```
Asn Ala Gly Met Val Asn Met Pro Thr Leu Ser Cys Ala Asn Gly Tyr
305                 310                 315                 320

Tyr Pro Ala Leu Thr Asn Val Asn Pro Tyr His Arg Leu Asp Thr Trp
                325                 330                 335

Lys Asp Thr Leu Asn His Trp Val Ala Tyr Pro Asp Met Leu Phe Tyr
                340                 345                 350

His Ser Val Ala Met Ile Glu Ser Cys Tyr Val Glu Leu Gly Asn Val
            355                 360                 365

Ala Arg Val Ser Asp Ser Asp Ala Ile Asn Lys Tyr Thr Phe Thr Glu
    370                 375                 380

Leu Ser Val Gln Gly Arg Pro Val Met Asn Arg Gly Ile Ile Val Asp
385                 390                 395                 400

Leu Thr Leu Val Ala Met Arg Thr Gly Arg Glu Ile Ser Leu Pro Tyr
                405                 410                 415

Pro Val Ser Cys Gly Leu Thr Arg Thr Asp Ala Leu Leu Gln Gly Thr
            420                 425                 430

Glu Ile His Val Pro Val Val Val Lys Asp Ile Asp Met Pro Gln Tyr
        435                 440                 445

Tyr Asn Ala Ile Asp Lys Val Ile Glu Gly Gln Glu Thr Val Ile
    450                 455                 460

Lys Val Lys Gln Leu Pro Pro Ala Met Tyr Pro Ile Tyr Thr Tyr Gly
465                 470                 475                 480

Ile Asn Thr Thr Glu Phe Tyr Ser Asp His Phe Glu Asp Gln Val Gln
                485                 490                 495

Val Glu Met Ala Pro Ile Asp Asn Gly Lys Ala Val Phe Asn Asp Ala
            500                 505                 510

Arg Lys Phe Ser Lys Phe Met Ser Ile Met Arg Met Met Gly Asn Asp
        515                 520                 525

Val Thr Ala Thr Asp Leu Val Thr Gly Arg Lys Val Ser Asn Trp Ala
    530                 535                 540

Asp Asn Ser Ser Gly Arg Phe Leu Tyr Thr Asp Val Lys Tyr Glu Gly
545                 550                 555                 560

Gln Thr Ala Phe Leu Val Asp Met Asp Thr Val Lys Ala Arg Asp His
                565                 570                 575

Cys Trp Val Ser Ile Val Asp Pro Asn Gly Thr Met Asn Leu Ser Tyr
            580                 585                 590

Lys Met Thr Asn Phe Arg Ala Ala Met Phe Ser Arg Asn Lys Pro Leu
        595                 600                 605

Tyr Met Thr Gly Gly Ser Val Arg Thr Ile Ala Thr Gly Asn Tyr Arg
    610                 615                 620

Asp Ala Ala Glu Arg Leu Arg Ala Met Asp Glu Thr Leu Arg Leu Lys
625                 630                 635                 640

Pro Phe Lys Ile Thr Glu Lys Leu Asp Phe Arg Val Ala Ala Tyr Ala
                645                 650                 655

Ile Pro Ser Leu Ser Gly Ser Asn Met Pro Ser Leu His His Gln Glu
            660                 665                 670

Gln Leu Gln Ile Ser Glu Val Asp Ala Glu Pro Ile Asn Pro Ile Gly
        675                 680                 685

Glu Asp Glu Leu Pro Pro Asp Ile Glu
690                 695
```

( 2 ) INFORMATION FOR SEQ ID NO:5:

( i ) SEQUENCE CHARACTERISTICS:
        ( A ) LENGTH: 40 base pairs ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GATCTATAAA GATGTCGGAT CCCCCGGGGG TACCGTCGAC 40